United States Patent
Landis

(10) Patent No.: US 11,879,883 B1
(45) Date of Patent: Jan. 23, 2024

(54) PRECIOUS METAL SOURCE VERIFICATION BY TRACE ELEMENTS

(71) Applicant: Samuel Landis, Stewart, FL (US)

(72) Inventor: Samuel Landis, Stewart, FL (US)

( * ) Notice: Subject to any disclaimer, the term of this patent is extended or adjusted under 35 U.S.C. 154(b) by 0 days.

(21) Appl. No.: 17/896,010

(22) Filed: Aug. 25, 2022

(51) Int. Cl.
*G01N 33/202* (2019.01)

(52) U.S. Cl.
CPC .................. *G01N 33/202* (2019.01)

(58) Field of Classification Search
None
See application file for complete search history.

(56) References Cited

U.S. PATENT DOCUMENTS

| 3,981,175 | A | * | 9/1976 | Hammond, III | ....... | G01N 25/18 |
| | | | | | | 374/10 |
| 4,385,843 | A | * | 5/1983 | Hammond, III | ....... | G01N 25/18 |
| | | | | | | 374/43 |
| 6,431,748 | B1 | * | 8/2002 | Baratta | .............. | G01N 33/2028 |
| | | | | | | 374/45 |
| 9,963,740 | B2 | | 5/2018 | Berrada et al. | | |
| 2013/0202084 | A1 | * | 8/2013 | Piorek | .................... | G01B 15/02 |
| | | | | | | 378/45 |
| 2014/0201033 | A1 | * | 7/2014 | Crain | .................. | G06Q 30/0609 |
| | | | | | | 705/26.35 |
| 2020/0230640 | A1 | | 7/2020 | Ruggiero | | |

FOREIGN PATENT DOCUMENTS

| CN | 111505105 | | 5/2020 | | |
| CN | 112326929 | | 10/2020 | | |
| GB | 2225114 | A * | 5/1990 | ............. | G01N 27/72 |
| JP | 2006329687 | | 5/2005 | | |
| WO | WO-0125747 | A2 * | 4/2001 | ........... | G01N 23/223 |

* cited by examiner

*Primary Examiner* — Daniel S Larkin

(57) ABSTRACT

A precious metal source verification system includes a quantity of precious metal being formed into a shape. A quantity of trace elements is imprinted into the shape with the precious metal such that the trace elements are detectible within the shape. The quantity of trace elements defines a signature for the shape. The quantity of trace elements is at least partially destroyed or altered upon melting of the shape wherein the signature is destroyed if the shape is altered. The system provides verification of provenance of the precious metal when the signature is maintained.

1 Claim, No Drawings

PRECIOUS METAL SOURCE VERIFICATION BY TRACE ELEMENTS

(b) CROSS-REFERENCE TO RELATED APPLICATIONS

Not Applicable

(c) STATEMENT REGARDING FEDERALLY SPONSORED RESEARCH OR DEVELOPMENT

Not Applicable

(d) THE NAMES OF THE PARTIES TO A JOINT RESEARCH AGREEMENT

Not Applicable

(e) INCORPORATION-BY-REFERENCE OF MATERIAL SUBMITTED ON A COMPACT DISC OR AS A TEXT FILE VIA THE OFFICE ELECTRONIC FILING SYSTEM.

Not Applicable

(f) STATEMENT REGARDING PRIOR DISCLOSURES BY THE INVENTOR OR JOINT INVENTOR

Not Applicable

(g) BACKGROUND OF THE INVENTION

(1) Field of the Invention

The disclosure relates to precious metal source verification devices and more particularly pertains to a new precious metal source verification device for using the introduction of trace elements to define a detectable signature.

(2) Description of Related Art Including Information Disclosed Under 37 CFR 1.97 and 1.98.

The prior art relates to precious metal source verification devices. What is lacking in known prior art is the introduction of a trace element signature during formation of a bar of precious metal such that detection of the signature may verify the bar remains unaltered since the formation at a particular source.

(h) BRIEF SUMMARY OF THE INVENTION

An embodiment of the disclosure meets the needs presented above by generally comprising a quantity of precious metal being formed into a shape. A quantity of trace elements is imprinted into the shape with the precious metal such that the trace elements are detectible within the shape. The quantity of trace elements defines a signature for the shape. The quantity of trace elements being at least partially destroyed or altered upon melting of the shape wherein the signature is destroyed if the shape is altered.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

(i) BRIEF DESCRIPTION OF SEVERAL VIEWS OF THE DRAWING(S)

Not Applicable

(j) DETAILED DESCRIPTION OF THE INVENTION

A new precious metal source verification device is described. A quantity of precious metal such as but not limited to gold, platinum, and silver, is formed into a shape such as an ingot or bar. A quantity of trace elements is imprinted into the shape with the precious metal. Imprinting, for purpose of the disclosure herein, is the incorporation of the trace elements into the shape such that the trace elements are detectible with the shape using conventional technology using one of X-ray fluorescence, mass spectrometry, or assay. Imprinting generally is the mixing and melting of the trace elements and the precious metal together, simultaneously or in parts as described below, to fully incorporate them as one unit. The trace elements are distributed evenly so that taking an assay or X-ray fluorescence reading anywhere on the shape should produces a consistent result. The consistent result as to the quantity of trace elements defines a signature for the shape. The signature remains unaltered while the shape remains in a solid state. At least some of the quantity of trace elements is removed from the signature upon melting of the shape. Thus, the signature is changed upon melting of the shape. This allows for verification that the shape has not been melted, adulterated, or altered when later tested for presence of the trace elements consistent with the signature imprinted upon formation of the shape. The signature may be at least five detectable elements. A total amount of the trace elements is less than 1000 parts per million of the shape to maintain 99.9% purity of the precious metal. Each trace element may be between 0.1 and 100 parts per million of the shape. The quantity of trace elements may include elements being lighter than iron on the periodic table. These elements generally are destroyed by heating to a temperature less than the melting point of the precious metal such that they will be destroyed upon melting of the shape. The signature would also be "destroyed" by the addition of more impurities, meaning any additional matter which is not the precious metal. Thus, reshaping of the shape or adding impurities to adulterate and lessen the overall content of the precious metal is detectable by use of the conventional technology described above and producing a result not matching the signature introduced upon formation of the shape.

In use, the above provides for a method of verifying a source of precious metal by imprinting the shape of formed precious metal with the quantity of trace elements to define the signature wherein the signature is altered by melting or sufficient heating of the shape. Imprinting may include melting of the precious metal and mixing the quantity of trace elements into the precious metal after melting such that the quantity of trace elements is evenly distributed throughout the precious metal. Thus, detection of the signature can be made on any portion of the shape formed. The imprinting may be achieved by melting the quantity of the trace elements simultaneously with the precious metal and mixing. Alternatively, imprinting may also be achieved by melting a first portion of the quantity of trace elements simultaneously with the precious metal to form a first mixture, then cooling the first mixture such that a second portion of the quantity of trace elements can be mixed with the first mixture without destroying the second portion of the quantity of trace elements. The second portion of the quantity of trace elements is mixed with the first mixture to form a second mixture which is then formed into the shape. The second portion of the quantity of trace elements would comprise elements lighter than iron on the periodic table as these would otherwise be destroyed prior to formation of the signature if melted simultaneously with the precious metal. As may be appreciated from the above description, the signature can be recorded and verified any later time using conventional technology such that matching of the signature insures no tampering, adulteration, or modification of the precious metal has occurred.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A method of verifying a precious metal source, the steps of the method comprising:
   imprinting a shape of formed precious metal with a quantity of trace elements defining a signature, the signature being altered by melting of the shape;
   wherein the imprinting includes melting of a precious metal and mixing the quantity of trace elements into the precious metal after melting wherein the quantity of trace elements is evenly distributed throughout the precious metal;
   wherein the mixing of the quantity of trace elements includes melting a first portion of the quantity of trace elements simultaneously with the precious metal to form a first mixture;
   cooling the first mixture such that a second portion of the quantity of trace elements can be mixed with the first mixture without destroying the second portion of the quantity of trace elements, mixing of the second portion of the quantity of trace elements with the first mixture to form a second mixture, the second portion of the quantity of trace elements comprising elements lighter than iron; and
   forming the shape from the second mixture.

* * * * *